(12) United States Patent
Baltcheva et al.

(10) Patent No.: US 11,951,101 B2
(45) Date of Patent: Apr. 9, 2024

(54) METHODS OF USING FACTOR B INHIBITORS

(71) Applicant: Novartis AG, Basel (CH)

(72) Inventors: Irina Baltcheva, Oberwil (CH); Peter End, Oberwil (CH); Julie Marie-Pomme Gabrielle Milojevic, Village Neuf (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/376,483

(22) Filed: Jul. 15, 2021

(65) Prior Publication Data

US 2022/0016103 A1 Jan. 20, 2022

Related U.S. Application Data

(60) Provisional application No. 63/052,705, filed on Jul. 16, 2020.

(51) Int. Cl.
*A61K 31/454* (2006.01)
*A61K 9/00* (2006.01)
*A61P 7/06* (2006.01)

(52) U.S. Cl.
CPC .......... *A61K 31/454* (2013.01); *A61K 9/0053* (2013.01); *A61P 7/06* (2018.01)

(58) Field of Classification Search
CPC .................................................. A61K 31/454
See application file for complete search history.

(56) References Cited

PUBLICATIONS

Schubart et al. CAS: 2003682473, 2019.*
Webb et al., "MO042 LNP023: A Novel Oral Complement Alternative Pathway Factor B Inhibitor for The Treatment of Glomerular Disease", p. MO042-MO042, (2020).
Risitano A M & Marotta S Ed., "Toward complement inhibition 2.0: Next generationanticomplement agents for paroxysmal nocturnalhemoglobinuria", Am. J. Hematol,,vol. 93, p. 564-577, (2018).
Schubart et al., "Small-molecule factor B inhibitor for the treatment of complement-mediated diseases", Proceedings of the National Academy of Sciences,vol. 116, No. 16 p. 7926-7931,(2019).
History of Changes for Study: NCT03439839, Study of Safety, Efficacy, Tolerability, Pharmaokinetics, and Pharmacodynamics of LNP023 in Patients with Paroxysmal Nocturnal Hemolobinuria (PNH), May 17, 2020 (6 pages).
Novartis AG Investor Relations, Q4 and FY 2019 Results Investor Presentation, Jan. 29, 2020 (6 pages).

* cited by examiner

*Primary Examiner* — Rei Tsang Shiao
(74) *Attorney, Agent, or Firm* — Timothy P. O'Dea

(57) ABSTRACT

Described herein are methods of treating paroxysmal nocturnal hemoglobinuria (PNH) with the Factor B inhibitor LNP023 or a pharmaceutically acceptable salt thereof, e.g. LNP023 hydrochloride.

38 Claims, 4 Drawing Sheets

FIG. 2

| Period | Screening | | Randomized treatment period | | | | | | | | | | | |
|---|---|---|---|---|---|---|---|---|---|---|---|---|---|---|
| Visit Name | Screening | Screening Hb confirmation | Day 1 | Day 7 | Day 14 | Day 28 | Day 42 | Day 56 | Day 84 | Day 112 | Day 126 | Day 140 | Day 154 | Day 168 |
| Days | -60 to -1 | -60 to -1 | 1 | 7 ±1 | 14 ±1 | 28 ±1 | 42 ±3 | 56 ±3 | 84 ±3 | 112 ±3 | 126 ±3 | 140 ±3 | 154 ±3 | 168 ±3 |
| Weeks | -8 to -1 | -8 to -1 | 1 | 1 | 2 | 4 | 6 | 8 | 12 | 16 | 18 | 20 | 22 | 24 |
| Informed consent | X | | | | | | | | | | | | | X |
| Entry criteria | X | X | | | | | | | | | | | | |
| Demography | X | | | | | | | | | | | | | |
| Medical history/current medical conditions | X | | | | | | | | | | | | | |
| Vaccination history & Vaccination | X | | | | | | | | | | | | | |
| Alcohol and Smoking history | X | | | | | | | | | | | | | |
| HIV | S | | | | | | | | | | | | | |
| Physical examination | S | | S | | | S | | | | | | | | S |
| Blood pressure and pulse rate | X | | X | X | X | X | X | X | X | X | X | X | X | X |
| Body height | X | | | | | | | | | | | | | |
| Body weight | X | | X | | | | | X | | X | | | | X |
| Body temperature | X | | X | X | X | X | X | X | X | X | X | X | X | X |
| Pregnancy test | S | | S | | | | | S | | | | | | S |
| Clinical Chemistry (full) | X | | X | | | | | X | | X | | | | X |
| Clinical Chemistry (abbreviated) | | | | X | X | X | X | | X | | X | X | X | |
| Hematology (full) | X | | X | | | X | | X | X | X | | X | | X |
| Hematology (abbreviated) | | X (Hb only) | | X | X | | X | | | | X | | X | |
| Coagulation/Markers of thrombosis | X | | X | | | X | | X | X | X | | X | | X |
| Panel of hormones blood samples | X | | X | | | X | | X | X | X | | X | | X |
| PNH clone size, C3+ RBC, PNH type RBC | X | | X | | | X | | X | | X | | X | | X |
| PK blood collection[1] | | | | X | | X | | X | | | | | | X |
| Urinalysis (dipstick) | X | | X | | | X | | X | | X | | X | | X |
| Urine Albumin/Creatinine ratio | | | X | | | | | | | X | | | | X |
| Breakthrough hemolysis | | | X | | | | | | | | | | | |
| PNH signs and symptoms | X | | X | X | X | X | X | X | X | X | X | X | X | X |

FIG. 2 (cont'd)

| Period | Screening | | Randomized treatment period | | | | | | | | | | | |
|---|---|---|---|---|---|---|---|---|---|---|---|---|---|---|
| Visit Name | Screening | Screening Hb confirmation | Day 1 | Day 7 | Day 14 | Day 28 | Day 42 | Day 56 | Day 84 | Day 112 | Day 126 | Day 140 | Day 154 | Day 168 |
| Days | -60 to -1 | -60 to -1 | 1 | 7 ±1 | 14 ±1 | 28 ±1 | 42 ±3 | 56 ±3 | 84 ±3 | 112 ±3 | 126 ±3 | 140 ±3 | 154 ±3 | 168 ±3 |
| Weeks | -8 to -1 | -8 to -1 | 1 | 1 | 2 | 4 | 6 | 8 | 12 | 16 | 18 | 20 | 22 | 24 |
| RBC transfusion | | | X | | | | | | | | | | | |
| 12-lead Electrocardiogram (ECG) | X | | X | | | | | | X | | | | | X |
| Adverse Events | | | X | | | | | | | | | | | |
| Major Adverse Vascular Events | | | X | | | | | | | | | | | |
| Concomitant medications | | | X | | | | | | | | | | | |
| ER visits / hospitalization | | | X | | | | | | | | | | | |
| Surgical and medical procedures | | | X | | | | | | | | | | | |
| Patient reported outcomes | | X[3] | X | X[4] | X | | X | | X | | X | X | X | X |
| IRT | X | X[2] | X | | | X | | X | X | X | | X | | X |
| LNP023 | | | b.i.d. | | | | | | | | | | | |
| Eculizumab | | | every 2 weeks | | | | | | | | | | | |
| Ravulizumab | | | X | | | | | | X | X | | | | X |
| Pharmacogenetic sample collection (optional) | | | X[5] | | | | | | | | | | | |
| Biomarker plasma/serum (optional) | | | X | | | | | | | | | | | X |
| Disposition | | | X | | | | | | | | | | | |

X = assessment to be recorded in the clinical database or received electronically from a vendor
S = assessment to be recorded in the source documentation only

[1] PK sample collection only for participants randomized to the LNP023 arm. These samples shall be taken pre-dose and approximately 2h post-dose
[2] Randomization after eligibility confirmed
[3] First PRO completion should occur after eligibility is confirmed and the participant is randomized
[4] Only FACIT-F and PGIS questionnaires will be carried out at this visit
[5] If the Pharmacogenetic-DNA sample is not taken at Day 1 visit, it can be taken at any visit thereafter

FIG. 3

| Period | Extension Period | | | | | | |
|---|---|---|---|---|---|---|---|
| Visit Name | [Day 182] *x-comparator only* ** | Day 196 | Day 224 | Day 258 | Day 280 | Day 308 | EOS |
| Days | 182 ± 3 | 196 ± 5 | 224 ± 5 | 258 ± 5 | 280 ± 5 | 308 ± 5 | 336 ± 5 |
| Weeks | 26 | 28 | 32 | 36 | 40 | 44 | 48 |
| Blood pressure and pulse rate | X | X | X | X | X | X | X |
| Physical examination | | | | | | | S |
| Body weight | | | | | | | X |
| Body temperature | X | X | X | X | X | X | X |
| Pregnancy test | | | | | | | S |
| Clinical Chemistry (full) | | | | X | | | X |
| Clinical Chemistry (abbreviated) | X | X | | | X | X | |
| Hematology (full) | | | X | X | X | X | X |
| Hematology (abbreviated) | X | X | | | | | |
| Coagulation/markers of thrombosis | | X | X | X | X | X | X |
| Panel of safety hormones blood samples | | X | X | | X | | X |
| PNH clone size, $C3^+$ RBC, PNH type RBC | | X | X | | X | | X |
| PK blood collection[1] | | X | X | | | | X |
| Urinalysis (dipstick) | X | X | X | X | X | X | X |
| Urine Albumin/Creatinine ratio | | | | X | | | X |
| Breakthrough hemolysis | X | | | | | | |
| PNH signs and symptoms | X | X | X | X | X | X | X |
| RBC transfusion | X | | | | | | |
| 12-lead Electrocardiogram (ECG) | | | | | | | X |
| Adverse Events | X | | | | | | |
| Major Adverse Vascular Events | X | | | | | | |
| Concomitant medications | X | | | | | | |
| ER visits / hospitalization | X | | | | | | |
| Surgical and medical procedures | X | | | | | | |
| Patient reported outcomes | | X | X | X | X | X | X |
| IRT | | X | X | X | X | X | X |
| LNP023 | b.i.d. from Day 169 | | | | | | |
| Disposition | X | | | | | | |

** Visit [Day 182] will be completed only by those participants that were taking comparator treatment on Week-24 visit and progressing into the Extension period
X = assessment to be recorded in the clinical database or received electronically from a vendor
S = assessment to be recorded in the source documentation only
[1]PK Sample collection-These samples shall be taken pre-dose and approximately 2h post-dose

METHODS OF USING FACTOR B INHIBITORS

CLAIM OF PRIORITY

This application claims priority to U.S. Provisional Patent Application No. 63/052,705 filed Jul. 16, 2020, which is incorporated herein by reference in its entirety.

FIELD

The disclosure relates to methods of treating complement driven diseases, and in particular, paroxysmal nocturnal hemoglobinuria (PNH) with the Factor B inhibitor LNP023 or a pharmaceutically acceptable salt thereof, e.g. LNP023 hydrochloride.

BACKGROUND

Paroxysmal nocturnal hemoglobinuria (PNH) is a rare acquired hemolytic disorder characterized by complement-mediated intravascular hemolysis, bone marrow failure (BMF) and severe thrombophilia (Risitano A M (2012). Paroxysmal nocturnal hemoglobinuria and other complement-mediated hematological disorders. Immunology; 217: 1080-1087). It begins with the clonal expansion of a hematopoietic stem cell that has acquired a somatic mutation in the phosphatidylinositol N-acetylglucosaminyltransferase subunit A (PIGA) gene (Brodsky R A (2014) Paroxysmal nocturnal hemoglobinuria. Blood; 124:2804-2811). Consequently, PNH blood cells lack the glycophosphatidylinositol (GPI) anchor protein and are deficient in the membrane-bound complement inhibitory proteins CD55 and CD59. As a result, PNH type red blood cells (RBCs) are attacked by complement leading to complement mediated lysis.

The clinical spectrum of PNH varies, and signs and symptoms include anemia, thrombosis, smooth muscle dystonia, fatigue, hemoglobinuria, chronic kidney disease and pulmonary hypertension. The clinical presentation is driven by uncontrolled complement activation on CD55 and CD59 deficient PNH type RBCs culminating with hemolysis and the release of free hemoglobin, and platelet activation (Hill A, et al. (2013). Thrombosis in paroxysmal nocturnal hemoglobinuria. Blood; 121:4985-4996). Hemolysis results in release of intracellular hemoglobin and lactate hydrogenase (LDH) into the circulation. Irreversible binding to and inactivation of nitric oxide (NO) by hemoglobin and inhibition of NO synthesis with consequent vasoconstriction and tissues ischemia, result in abdominal pain, dysphagia, erectile dysfunction, platelet activation and a prothrombotic status (Hill et al 2013, Brodsky 2014). Thromboembolism is the leading cause of morbidity and mortality in patients with PNH and can occur at any site; although venous is more common (80-85%), it can also be arterial (15-20%) (Hillmen P, et al. (2007). Effect of the complement inhibitor eculizumab on thromboembolism in patients with paroxysmal nocturnal hemoglobinuria. Blood; 110:4123-4128).

Eculizumab and ravulizumab (engineered from eculizumab with prolonged dosing interval) are approved anti-C5 antibody therapies for the treatment of PNH and the current standard of care (SoC) where available. Although the anti-C5 antibody therapy is generally effective in treating intravascular hemolysis (IVH), there remains a high-unmet medical need for PNH. Different authors reported heterogeneous hematological response with eculizumab and a substantial proportion of patients not achieving normal or near normal hemoglobin levels (Risitano A M, et al (2009) Complement fraction 3 binding on erythrocytes as additional mechanism of disease in paroxysmal nocturnal hemoglobinuria patients treated by eculizumab. Blood; 113:4094-4100; Hill A, et al. (2010). Eculizumab prevents intravascular hemolysis in patients with paroxysmal nocturnal hemoglobinuria and unmasks low-level extravascular hemolysis occurring through C3 opsonization. Haematologica; 95:567-573; DeZern A E, et al. (2013). Predictors of hemoglobin response to eculizumab therapy in paroxysmal nocturnal hemoglobinuria. Eur J Haematol; 90: 16-24; McKinley C. (2017) Extravascular Hemolysis Due to C3-Loading in Patients with PNH Treated with Eculizumab: Defining the Clinical Syndrome. ASH meeting abstract. Blood; 130 (Supplement1):3471). The heterogeneous response to eculizumab or other anti-C5 antibody treatment can be explained, in part, through its mechanism of action inhibiting only the terminal part of the complement cascade. Therefore, deposition of C3 fragments on the cell surface of PNH type erythrocytes lacking CD55 is not impacted, rendering the cells susceptible to extravascular hemolysis. Extracellular hemolysis can become the main mechanism of hemolysis in patients treated with eculizumab (Risitano et al 2009) and C3 mediated extravascular hemolysis represents an unmet medical need.

LNP023 is a novel, oral, small molecule compound that inhibits factor B (FB) and is in clinical development for the treatment of PNH. Factor B (FB) is a key protease of the complement alternative pathway (AP). Inhibition of FB with oral LNP023 or a pharmaceutically acceptable salt thereof, e.g., LNP023 hydrochloride, has the potential to prevent both intra- and extravascular hemolysis, and therefore, offer therapeutic benefits over and above the current standard of care (SoC). Additionally, the oral route of administration offers patients an advantage compared to the intravenous route of administration of current SoCs.

SUMMARY

The disclosure relates to methods of treating complement driven diseases, and in particular, paroxysmal nocturnal hemoglobinuria (PNH) with LNP023 or a pharmaceutically acceptable salt thereof, e.g. LNP023 hydrochloride. LNP023 belongs to the class of Factor B inhibitors of the complement pathway and acts by inhibiting or suppressing the amplification of the complement system caused by C3 activation irrespective of the initial mechanism of activation. LNP023 hydrochloride is currently in clinical development for the treatment of paroxysmal nocturnal hemoglobinuria (PNH). LNP023 hydrochloride is chemically designated as 4-((2S, 4S)-(4-ethoxy-1-((5-methoxy-7-methyl-1H-indol-4-yl) methyl)piperidin-2-yl))benzoic acid hydrochloride and can be represented by the following chemical structure:

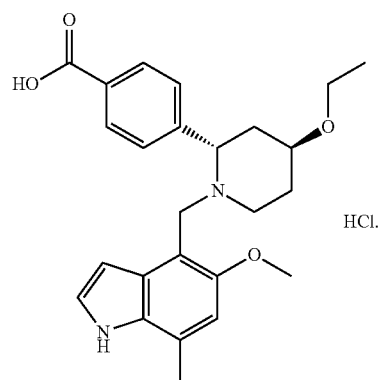 [SMILES: CCO[C@H]1CCN(Cc2c(OC)cc(C)c3[nH]ccc23)[C@H](c2ccc(C(=O)O)cc2)C1 ; "HCl."]

LNP023 hydrochloride and methods for its preparation are disclosed in WO2015/009616 (see Example 26d), which is incorporated herein by reference in its entirety.

In one aspect, the disclosure provides a method of treating paroxysmal nocturnal hemoglobinuria (PNH) in a subject, e.g., a patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours, to thereby treat the subject, e.g., patient (wherein the dosing amount refers to the anhydrous free base of LNP023 hydrochloride), to thereby treat the subject, e.g., a patient.

In another aspect, the disclosure provides a method of treating PNH associated hemolysis in a subject, e.g., a patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours, to thereby treat the subject, e.g., patient (wherein the dosing amount refers to the anhydrous free base of LNP023 hydrochloride), to thereby treat the subject, e.g., a patient.

In another aspect, the disclosure provides a method of normalizing intravascular hemolysis (IVH) and/or extravascular hemolysis (EVH) in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby normalize IVH and/or EVH the subject, e.g., a patient.

In another aspect, the disclosure provides a method of reducing the rate of occurrence of PNH associated hemolysis in a patient population, the method comprising orally administering to the patients LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby reduce the rate of occurrence.

In another aspect, the disclosure provides a method of treating intravascular hemolysis (IVH), e.g., controlling IVH, in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., a patient.

In another aspect, the disclosure provides a method of treating extravascular hemolysis (EVH), e.g., controlling EVH, in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., a patient.

In another aspect, the disclosure provides a method of normalizing hemoglobin levels in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby normalize hemoglobin levels in the subject, e.g., a patient.

In another aspect, the disclosure provides a method of reducing C3 deposition in a subject in need thereof, the method comprising orally administering to the subject, e.g., a patient, LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby reduce C3 deposition in the subject, e.g., a patient.

In another aspect, the disclosure provides a method of increasing red blood cell (RBC) survival, e.g., increasing the lifetime of RBCs, in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby increase RBC survival in the subject, e.g., a patient.

In another aspect, the disclosure provides a method of inhibiting the complement alternative pathway, e.g., sustaining inhibition, in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby inhibit the complement alternative pathway in the subject, e.g., a patient.

In another aspect, the disclosure provides a method of reducing Fragment Bb levels in a subject, e.g., a patient, in need thereof, the method comprising orally administering to the subject LNP023 or a pharmaceutically acceptable salt thereof, e.g. LNP023 hydrochloride, at a dose of about 200 mg twice daily (b.i.d.), e.g., about every 12 hours (wherein the dosing amount refers to the anhydrous free base of LNP023 hydrochloride), to thereby reduce Fragment Bb in the subject, e.g., a patient.

Treatment methods described herein can additionally comprise various evaluation steps prior to and/or following treatment with LNP023 or a pharmaceutically acceptable salt thereof, e.g. LNP023 hydrochloride. In an embodiment, prior to and/or after administration of LNP023 or a pharmaceutically acceptable salt thereof, e.g. LNP023 hydrochloride, the methods further comprise the step of evaluating PK and PD parameters (e.g., plasma concentration of LNP023 or a pharmaceutically acceptable salt thereof, e.g. LNP023 hydrochloride, C3, Fragment Bb, or sC5B). Evaluation may be achieved by sample analysis of bodily fluid, such as blood or plasma by e.g., mass spectroscopy, e.g. LC-MS.

BRIEF DESCRIPTION OF THE DRAWINGS

FIG. 2 is a table of the assessment schedule during the randomized treatment period.

FIG. 3 is a table of the assessment schedule during the extension period.

DETAILED DESCRIPTION

Figure 1:
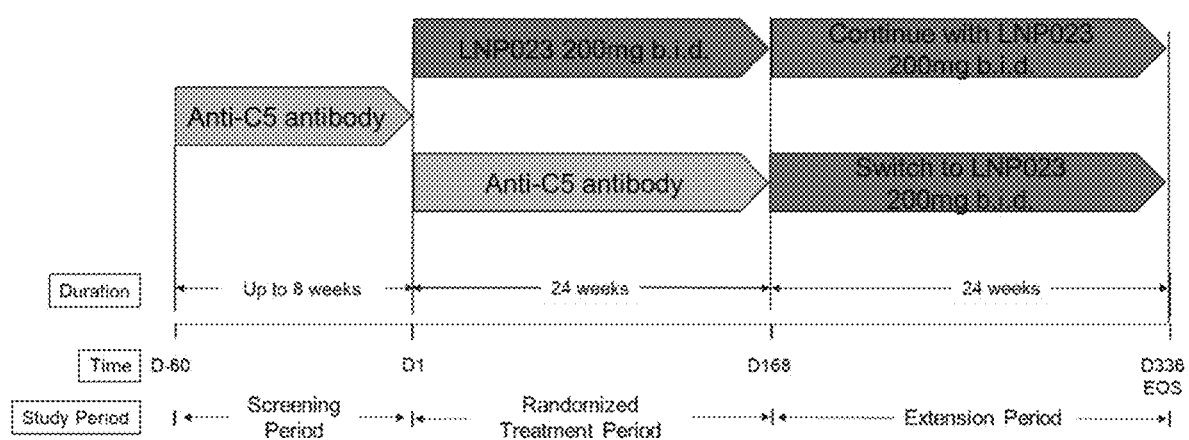
FIG. 1 depicts a schematic of the study design.

Described herein is the Phase 3 clinical study to determine safety and efficacy of LNP023 or a pharmaceutically acceptable salt thereof, e.g., LNP023 hydrochloride, in patients with PNH presenting with residual anemia despite treatment with anti-C5 therapy. Accordingly, described herein are methods of treating PNH in a patient in need thereof, the method comprising orally administering, e.g., in capsule form, to the patient a twice daily dose, e.g., about every 12 hours, of LNP023 or a pharmaceutically acceptable salt thereof, e.g., LNP023 hydrochloride, (wherein the dosing amount refers to the anhydrous free base of LNP023 hydrochloride). Also described herein are methods of selecting the target patient population, methods of monitoring treatment of the target patient population, and methods of assessing safety and efficacy of treatment of the target patient population.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Remington's Pharmaceutical Sciences," Mack Publishing Co., Easton, Pa., 21st edition, 2005, which is hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "about" means within ±10% of a value.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent.

As used herein, the term "acquire" or "acquiring" as the terms are used herein, refer to obtaining possession of a physical entity (e.g., a sample, e.g., a blood sample or a blood plasma sample), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g. LC-MS, e.g., LC-MS/MS methods.

As used herein, "dose" means a specified quantity of a pharmaceutical agent provided in a single administration, or in a specified time period. In certain embodiments, a dose can be administered in capsules. As used herein, the dosing amount refers to the anhydrous free base of LNP023 hydrochloride.

As used herein, "individual", "patient", "participant", or "subject" means a human selected for treatment or therapy.

As used herein, "pharmaceutically acceptable salts" means physiologically and pharmaceutically acceptable salts of LNP023, i.e., salts that retain the desired biological activity of LNP023 and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of LNP023 may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). LNP023 hydrochloride and methods for its preparation are disclosed in WO2015/009616 (see Example 26d), which is incorporated herein by reference in its entirety.

As used herein, the term "treat" means decrease, suppress, attenuate, diminish, arrest, or stabilize the development or progression of a disorder or disease, e.g., PNH.

Unless otherwise specified, conventional definitions of terms control and conventional stable atom valences are presumed and achieved in all formulas and groups.

The articles "a" and "an" are used in this disclosure to refer to one or more than one (e.g., to at least one) of the grammatical object of the article. By way of example, "an element" means one element or more than one element.

Methods of Use

Provided herein is a method of treating paroxysmal nocturnal hemoglobinuria (PNH) in a subject, e.g., a patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has been treated with an anti-C5 therapy.

In an embodiment, the subject, e.g., patient, has been treated with an anti-C5 therapy for at least about 8 months prior to administration of LNP023 or a pharmaceutically acceptable salt thereof, e.g., LNP023 hydrochloride.

In an embodiment, the subject, e.g., patient, has been treated with an anti-C5 therapy for at least about 6 months prior to administration of LNP023 or a pharmaceutically acceptable salt thereof, e.g., LNP023 hydrochloride.

In an embodiment, the anti-C5 therapy is an anti-C5 monoclonal antibody therapy.

In an embodiment, the anti-C5 therapy is eculizumab or ravulizumab.

In an embodiment, the subject, e.g., patient, has residual anemia.

In an embodiment, the subject, e.g., patient, has been vaccinated prior to treatment with LNP023 or a pharmaceutically acceptable salt thereof, e.g., LNP023 hydrochloride.

In an embodiment, the subject, e.g., patient, has been vaccinated against *Neisseria meningitidis* (types A, C, Y and W-135) prior to treatment.

In an embodiment, treating PNH comprises increasing hemoglobin levels in the subject, e.g., patient, in the absence of receiving one or more red blood cell (RBC) transfusion(s).

In an embodiment, the subject, e.g., patient, has received RBC transfusions, e.g., at least 1 packed-RBC transfusion(s), e.g., about 6 months prior to administration of LNP023 or a pharmaceutically acceptable salt thereof, e.g. LNP023 hydrochloride.

In an embodiment, hemoglobin levels in the subject, e.g., patient, are evaluated prior to administration of LNP023 or a pharmaceutically acceptable salt thereof, e.g., LNP023 hydrochloride.

In an embodiment, hemoglobin levels, haptoglobin levels, reticulocyte levels, and/or bilirubin levels of the subject, e.g., patient, are evaluated prior to administration of LNP023 or a pharmaceutically acceptable salt thereof, e.g. LNP023 hydrochloride.

In an embodiment, hemoglobin levels in the subject, e.g., patient, are less than about 12 g/dL, less than about 11.5 g/dL, less than about 11 g/dL, less than about 10.5 g/dL, less than about 10 g/dL, less than about 9.5 g/dL, less than about 9 g/dL, less than about 8.5 g/dL, or less than about 8 g/dL, prior to treatment with LNP023 or a pharmaceutically acceptable salt thereof, e.g., LNP023 hydrochloride.

In an embodiment, the hemoglobin levels of the subject, e.g., patient, are less than or equal to about 10 g/dL, prior to administration of LNP023 hydrochloride.

In an embodiment, hemoglobin levels in the subject, e.g., patient, are increased, e.g., by about 1 g/dL or more, about 1.5 g/dL 2 g/dL, about 2.5 g/dL or more, or about 3 g/dL or more, after treatment with LNP023 or a pharmaceutically acceptable salt thereof, e.g., LNP023 hydrochloride, e.g., as compared to baseline, e.g., as compared to hemoglobin levels prior to treatment with LNP023 or a pharmaceutically acceptable salt thereof, e.g., LNP023 hydrochloride.

In an embodiment, hemoglobin levels in the subject, e.g., patient, are increased by about 2 g/dL or more, e.g., as compared to baseline, e.g., as compared to hemoglobin levels prior to treatment with LNP023 or a pharmaceutically acceptable salt thereof, e.g., LNP023 hydrochloride.

In an embodiment, treating PNH comprises normalizing intravascular hemolysis (IVH) and/or extravascular hemolysis (EVH) in the subject, e.g., patient. In an embodiment, normalizing IVH and/or EVH hemolysis comprises increasing the haptoglobin level, decreasing reticulocytes level, or decreasing bilirubin level, in the subject, e.g., patient, e.g., as compared to baseline, e.g., as compared to the level of haptoglobin, reticulocytes, or bilirubin in the subject, e.g., patient, prior to administration of LNP023 or a pharmaceutically acceptable salt thereof, e.g. LNP023 hydrochloride.

In an embodiment, treating PNH comprises treating PNH associated hemolysis.

In an embodiment, treating PNH comprises reducing C3 deposition in the subject, e.g., patient. In an embodiment, C3 deposition is reduced by about 30%, about 35%, about 40%, about 45%, about 50%, about 55%, about 60%, about 65%, about 70%, about 75%, about 80%, about 85%, about 90%, about 95%, about 98%, or about 99%, e.g., as compared to baseline, e.g., as compared to the level of C3 deposition in the subject, e.g., patient, prior to administration of LNP023 or a pharmaceutically acceptable salt thereof, e.g. LNP023 hydrochloride.

In an embodiment, treating PNH comprises increasing red blood cell (RBC) survival in the subject, e.g., patient.

In an embodiment, treating PNH comprises inhibiting the complement alternative pathway in the subject, e.g., patient.

In an embodiment, treating PNH comprises reducing Fragment Bb levels in the subject, e.g., patient.

In an embodiment, treating PNH comprises increasing hemoglobin levels in the subject, e.g., patient, e.g., by about 2 g/dL or more, e.g., as compared to baseline, e.g., as compared to hemoglobin levels in the subject, e.g., patient, prior to administration of LNP023 or a pharmaceutically acceptable salt thereof, e.g. LNP023 hydrochloride.

In an embodiment, treating PNH comprises achieving a sustained increase in hemoglobin levels. In an embodiment, treating PNH comprises achieving a sustained increase in hemoglobin levels to greater than about 10 g/dL, greater than about 10.5 g/dL, greater than about 11 g/dL, greater than about 11.5 g/dL, greater than about 12 g/dL, greater than about 12.5 g/dL, or greater than about 13 g/dL. In an embodiment, treating PNH comprises achieving a sustained increase in hemoglobin levels to greater than or equal to about 12 g/dL.

In an embodiment, treating PNH comprises achieving a sustained increase in hemoglobin levels from baseline is about 1.5 g/dL or more, about 2 g/dL or more, about 2.5 g/dL or more, about 3 g/dL or more, about 3.5 g/dL or more, about 4 g/dL or more, about 4.5 g/dL or more, or about 5 g/dL or more, e.g., as compared to the hemoglobin levels in the patient prior to treatment with LNP023 or a pharmaceutically acceptable salt thereof, e.g. LNP023 hydrochloride.

In an embodiment, treating PNH comprises achieving a sustained increase in hemoglobin levels from baseline is about 2 g/dL or more, e.g., as compared to the hemoglobin levels in the patient prior to treatment with LNP023 or a pharmaceutically acceptable salt thereof, e.g. LNP023 hydrochloride.

In an embodiment, the increase in hemoglobin levels is sustained after about 1 week, after about 2 weeks, after about 3 weeks, after about 4 weeks, after about 6 weeks, after about 8 weeks, after about 10 weeks, after about 12 weeks, after about 14 weeks, after about 16 weeks, after about 18 weeks, after about 20 weeks, after about 22 weeks, or after about 24 weeks of administration of LNP023 or a pharmaceutically acceptable salt thereof, e.g., LNP023 hydrochloride.

In an embodiment, the increase in hemoglobin levels is sustained after about 18 to 24 weeks of administration of LNP023 or a pharmaceutically acceptable salt thereof, e.g., LNP023 hydrochloride.

In an embodiment, the increase in hemoglobin levels is sustained after about 18 or 24 weeks of administration of LNP023 or a pharmaceutically acceptable salt thereof, e.g., LNP023 hydrochloride.

In an embodiment, efficacy of treatment is determined by measuring the hemoglobin levels in the subject, e.g., patient, e.g., as compared to baseline, e.g., as compared to hemoglobin levels in the subject, e.g., patient, prior to administration of LNP023 or a pharmaceutically acceptable salt thereof, e.g., LNP023 hydrochloride.

In an embodiment, hemoglobin levels are increased by about 1.5 g/dL or more, about 2 g/dL or more, about 2.5 g/dL or more, about 3 g/dL or more, about 3.5 g/dL or more, about 4 g/dL or more, about 4.5 g/dL or more, or about 5 g/dL or more, e.g., as compared to hemoglobin levels in the subject, e.g., patient, prior to administration of LNP023 or a pharmaceutically acceptable salt thereof, e.g., LNP023 hydrochloride.

In an embodiment, hemoglobin levels are increased by about 2 g/dL or more, as compared to baseline, e.g., as compared to hemoglobin levels in the subject, e.g., patient, prior to administration of LNP023 or a pharmaceutically acceptable salt thereof, e.g., LNP023 hydrochloride.

In another aspect, the disclosure provides a method of normalizing intravascular hemolysis (IVH) and/or extravascular hemolysis (EVH) in a subject, e.g., patient, in need thereof, the method comprising orally administering to the subject, e.g., patient, LNP023 hydrochloride at a dose of about 200 mg twice daily (b.i.d.), e.g., about every 12 hours (wherein the dosing amount refers to the anhydrous free base of LNP023 hydrochloride), to thereby normalize IVH and/or EVH, in the subject, e.g., patient.

In an embodiment, the subject, e.g., patient, has or is diagnosed as having PNH.

In an embodiment, normalizing IVH and/or EVH hemolysis comprises increasing the haptoglobin level, decreasing reticulocytes level, or decreasing bilirubin level, in the subject, e.g., patient, e.g., as compared to baseline, e.g., as compared to the level of haptoglobin, reticulocytes, or bilirubin in the subject, e.g., patient, prior to administration of LNP023 or a pharmaceutically acceptable salt thereof, e.g., LNP023 hydrochloride.

In an embodiment, the level of haptoglobin is increased by about 10%, about 15%, about 20%, about 25%, about 30%, about 35%, about 40%, about 45%, about 50%, about 55%, about 60%, about 65%, about 70%, about 75%, about 80%, about 85%, or about 90%.

In an embodiment, the level of bilirubin or reticulocytes is reduced by about 10%, about 15%, about 20%, about 25%, about 30%, about 35%, about 40%, about 45%, about 50%, about 55%, about 60%, about 65%, about 70%, about 75%, about 80%, about 85%, or about 90%.

In an embodiment, the haptoglobin level, reticulocytes level, or bilirubin level in the subject, e.g., patient, is acquired by sample analysis of a bodily fluid, such as blood or plasma.

In another aspect, the disclosure provides a method of treating PNH associated hemolysis in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the PNH associated hemolysis is breakthrough hemolysis (BTH), e.g., as defined in Table 2.

In another aspect, the disclosure provides a method of reducing the rate of occurrence of PNH associated hemolysis in a patient population, the method comprising orally administering to the subject, e.g., patient, LNP023 or a pharmaceutically acceptable salt thereof, e.g., LNP023 hydrochloride, or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby reduce the rate of occurrence.

In an embodiment, the PNH associated hemolysis is breakthrough hemolysis (BTH), e.g., as defined in Table 2.

In an embodiment, the rate of occurrence is reduced by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In another aspect, the disclosure provides a method of treating intravascular hemolysis (IVH), e.g., controlling IVH, in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has or is diagnosed as having PNH.

In an embodiment, treating IVH, e.g., controlling IVH, comprises reducing the level of lactate hydrogenase (LDH) in the subject, e.g., patient, e.g., as compared to baseline, e.g., as compared to the level of LDH in the subject, e.g., patient, prior to administration of LNP023 or a pharmaceutically acceptable salt thereof, e.g., LNP023 hydrochloride.

In an embodiment, the LDH level in the subject, e.g., patient, is acquired by sample analysis of a bodily fluid, such as blood or plasma.

In an embodiment, the LDH level in the subject, e.g., patient, is reduced by at least about 40%, at least about 45%, at least about 50%, at least about 55%, at least about 60%, at least about 65%, at least about 70%, at least about 75%, or at least about 80%. In an embodiment, the LDH level in the subject, e.g., patient, is reduced by at least about 50%, at least about 55%, at least about 60%, at least about 65%, or at least about 70%. In an embodiment, the LDH level in the subject, e.g., patient, is reduced by at least about 60%.

In another aspect, the disclosure provides a method of treating extravascular hemolysis (EVH), e.g., controlling EVH, in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has or is diagnosed as having PNH.

In an embodiment, treating EVH, e.g., controlling EVH, comprises reducing the level of bilirubin or reticulocytes in the subject, e.g., patient, or increasing the level of haptoglobin, e.g., as compared to baseline, e.g., as compared to the level of bilirubin or reticulocytes in the subject, e.g., patient, prior to administration of LNP023 or a pharmaceutically acceptable salt thereof, e.g., LNP023 hydrochloride.

In an embodiment, the level of bilirubin or reticulocytes is reduced by about 10%, about 15%, about 20%, about 25%, about 30%, about 35%, about 40%, about 45%, about 50%, about 55%, about 60%, about 65%, about 70%, about 75%, about 80%, about 85%, or about 90%.

In an embodiment, the level of haptoglobin is increased by about 10%, about 15%, about 20%, about 25%, about 30%, about 35%, about 40%, about 45%, about 50%, about 55%, about 60%, about 65%, about 70%, about 75%, about 80%, about 85%, or about 90%.

In an embodiment, the value for the level of bilirubin, reticulocytes, or haptoglobin in the subject, e.g., patient, is acquired by sample analysis of a bodily fluid, such as blood or plasma.

In another aspect, the disclosure provides a method of normalizing hemoglobin levels in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby normalize hemoglobin levels in the subject, e.g., patient.

In an embodiment, hemoglobin levels are normalized, to greater than about 10 g/dL, to greater than about 10.5 g/dL, to greater than about 11 g/dL, to greater than about 11.5 g/dL, to greater than about 12 g/dL, to greater than about 12.5 g/dL, or to greater than about 13 g/dL.

In an embodiment, hemoglobin levels are normalized, to greater than or equal to about 12 g/dL.

In an embodiment, the subject, e.g., patient, has or is diagnosed as having PNH.

In an embodiment, normalizing hemoglobin levels occurs in the absence of a red blood cell transfusion.

In another aspect, the disclosure provides a method of reducing C3 deposition in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has or is diagnosed as having PNH.

In an embodiment, C3 deposition is reduced by about 30%, about 35%, about 40%, about 45%, about 50%, about 55%, about 60%, about 65%, about 70%, about 75%, about 80%, about 85%, about 90%, about 95%, about 98%, or about 99%.

In an embodiment, C3 deposition is fully reversed. In an embodiment, C3 deposition is quantified by flow cytometry as C3-fragment deposition on erythrocytes.

In another aspect, the disclosure provides a method of increasing red blood cell survival in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has or is diagnosed as having PNH.

In another aspect, the disclosure provides a method of inhibiting the complement alternative pathway, e.g., to achieve sustained inhibition, in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In an embodiment, the subject, e.g., patient, has or is diagnosed as having PNH.

In an embodiment, sustained inhibition of the complement alternative pathway is achieved after about 1 week, after about 2 weeks, after about 3 weeks, after about 4 weeks, after about 6 weeks, after about 8 weeks, after about 10 weeks, after about 12 weeks, after about 14 weeks, after about 16 weeks, after about 18 weeks, after about 20 weeks, after about 22 weeks, or after about 24 weeks of administration of LNP023 or a pharmaceutically acceptable salt thereof, e.g., LNP023 hydrochloride.

In an embodiment, sustained inhibition of the complement alternative pathway is achieved after about 18 to 24 weeks of administration of LNP023 or a pharmaceutically acceptable salt thereof, e.g., LNP023 hydrochloride.

In an embodiment, sustained inhibition of the complement alternative pathway is achieved after about 18 or 24 weeks of administration of LNP023 or a pharmaceutically acceptable salt thereof, e.g., LNP023 hydrochloride.

In another aspect, the disclosure provides a method of reducing Fragment Bb in a subject, e.g., patient, in need thereof, the method comprising orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby reduce Fragment Bb in the subject, e.g., patient.

In an embodiment, the subject, e.g., patient, has or is diagnosed as having PNH.

In an embodiment, Fragment Bb is reduced by about 30%, about 35%, about 40%, about 45%, about 50%, about 55%, about 60%, about 65%, about 70%, about 75%, about 80%, about 85%, or about 90%.

In another aspect, the disclosure provides LNP023 or a pharmaceutically acceptable salt thereof, e.g., LNP023 hydrochloride, for use in the treatment of paroxysmal nocturnal hemoglobinuria (PNH) in a subject, e.g., a patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In another aspect, the disclosure provides LNP023 or a pharmaceutically acceptable salt thereof, e.g., LNP023 hydrochloride, for use in the treatment of, e.g., the control of, intravascular hemolysis (IVH) and/or extravascular hemolysis (EVH) in a subject, e.g., patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby normalize IVH and/or EVH, in the subject, e.g., patient.

In an embodiment, the subject, e.g., patient, has or is diagnosed as having PNH.

In another aspect, the disclosure provides LNP023 or a pharmaceutically acceptable salt thereof, e.g., LNP023 hydrochloride, for use in the treatment of PNH associated hemolysis in a subject, e.g., patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In another aspect, the disclosure provides use of LNP023 or a pharmaceutically acceptable salt thereof, e.g., LNP023 hydrochloride, in the manufacture of a medicament for the treatment of paroxysmal nocturnal hemoglobinuria (PNH) in a subject, e.g., a patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

In another aspect, the disclosure provides use of LNP023 or a pharmaceutically acceptable salt thereof, e.g., LNP023 hydrochloride, in the manufacture of a medicament for the treatment of, e.g., the control of, intravascular hemolysis (IVH) and/or extravascular hemolysis (EVH) in a subject, e.g., patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby normalize IVH and/or EVH, in the subject, e.g., patient.

In an embodiment, the subject, e.g., patient, has or is diagnosed as having PNH.

In another aspect, the disclosure provides use of LNP023 or a pharmaceutically acceptable salt thereof, e.g., LNP023 hydrochloride, in the manufacture of a medicament for the treatment of PNH associated hemolysis in a subject, e.g., patient, in need thereof, wherein the treatment comprises orally administering to the subject, e.g., patient, LNP023 or a pharmaceutically acceptable salt thereof, e.g., LNP023 hydrochloride, at a dose of about 200 mg twice daily (b.i.d.), e.g., about every 12 hours (wherein the dosing amount refers to the anhydrous free base of LNP023 hydrochloride), to thereby treat the subject, e.g., patient.

Patient Selection and Monitoring

The Phase 3 study will enroll PNH patients with diagnosis confirmed by high-sensitivity flow cytometry (clone size of ≥10%) who despite being treated with SoC (eculizumab or ravulizumab) experience residual anemia defined as hemoglobin ≤10 g/dL, with or without regular red blood cell transfusions in the past 6 months. PNH blood cells lack the glycophosphatidylinositol (GPI) anchor protein (GPI-AP) and are deficient in the membrane-bound complement inhibitory proteins CD55 and CD59. The absence of these two GPI-APs, CD55 and CD59, leads to uncontrolled complement activation that accounts for hemolysis and other PNH manifestations. The rationale for selecting this patient population is that these patients present with unmet medical need despite SoC treatment.

LNP023 or a pharmaceutically acceptable salt thereof, e.g., LNP023 hydrochloride, can inhibit complement activation. Accordingly, a subject, e.g., a patient, can be selected for treatment with LNP023 or a pharmaceutically acceptable salt thereof, e.g., LNP023 hydrochloride, by first evaluating the patient to determine whether the subject, e.g., patient, has GPI-AP deficient blood cells, e.g., peripheral blood cells, and if the subject, e.g., patient, is determined to have GPI-AP deficient peripheral blood cells, then optionally administering to the subject, e.g., patient, LNP023 or a pharmaceutically acceptable salt thereof, e.g., LNP023 hydrochloride.

In an embodiment, high-sensitivity flow cytometry is used to determine whether the patient has GPI-AP deficient peripheral blood cells, e.g., in about 2 or more cell lineages.

In an embodiment, the subject, e.g., patient, can be monitored by evaluating certain PK/PD parameters, such as the level of LNP023 or a pharmaceutically acceptable salt thereof, e.g., LNP023 hydrochloride, the level of LDH, the level of hemoglobin, and PNH clone size.

Efficacy Assessment

Also provided herein is a method of assessing the efficacy of treatment in a patient population treated with LNP023 or a pharmaceutically acceptable salt thereof, e.g., LNP023 hydrochloride, at a dose of about 200 mg twice daily (b.i.d.), e.g., about every 12 hours, the method comprising determining the percentage of the patient population achieving an increase, e.g., a sustained increase, in hemoglobin levels as compared to baseline, to thereby assess efficacy of treatment, wherein baseline is the level of hemoglobin in a patient population prior to administration of LNP023 or a pharmaceutically acceptable salt thereof, e.g., LNP023 hydrochloride.

In an embodiment, the increase, e.g., sustained increase, in hemoglobin levels from baseline is about 1.5 g/dL or more, about 2 g/dL or more, about 2.5 g/dL or more, about 3 g/dL or more, about 3.5 g/dL or more, about 4 g/dL or more, about 4.5 g/dL or more, or about 5 g/dL or more. In an embodiment, the increase, e.g., sustained increase, in hemoglobin levels from baseline is about 2 g/dL or more, e.g., as compared to the hemoglobin levels in the patient prior to treatment with LNP023 or a pharmaceutically acceptable salt thereof, e.g., LNP023 hydrochloride.

In an embodiment, the increase in hemoglobin levels is sustained for at least about 18 weeks after administration of LNP023 or a pharmaceutically acceptable salt thereof, e.g., LNP023 hydrochloride. In an embodiment, the increase in hemoglobin levels is sustained for at least about 24 weeks after administration of LNP023 or a pharmaceutically acceptable salt thereof, e.g., LNP023 hydrochloride.

In an embodiment, the increase in hemoglobin levels is sustained for at least about 1 month, at least about 2 months, at least about 3 months, at least about 4 months, at least about 5 months, at least about 6 months, at least about 8 months, at least about 10 months, or at least about 12 months after administration of LNP023 or a pharmaceutically acceptable salt thereof, e.g., LNP023 hydrochloride.

In an embodiment, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of the patient population has achieved an increase, e.g., a sustained increase, in hemoglobin levels, e.g., as compared to the hemoglobin levels in the patient prior to treatment with LNP023 or a pharmaceutically acceptable salt thereof, e.g., LNP023 hydrochloride.

In an embodiment, the patients have or are diagnosed as having PNH.

In another aspect, the disclosure provides a method of assessing efficacy of treatment in a population of patients treated with LNP023 or a pharmaceutically acceptable salt thereof, e.g., LNP023 hydrochloride, at a dose of about 200 mg twice daily (b.i.d.), e.g., about every 12 hours, the method comprising determining the percentage of the population of patients achieving hemoglobin levels of, e.g., about 12 g/dL or more, to thereby assess efficacy of treatment.

In an embodiment, the patients have or are diagnosed as having PNH.

In an embodiment, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of the patient population has achieved an increase, e.g., a sustained increase, in hemoglobin levels, e.g., as compared to the hemoglobin levels in the patient prior to treatment with LNP023 or a pharmaceutically acceptable salt thereof, e.g., LNP023 hydrochloride.

In an embodiment, the increase in hemoglobin levels is sustained for at least about 18 weeks after administration of LNP023 or a pharmaceutically acceptable salt thereof, e.g., LNP023 hydrochloride. In an embodiment, the increase in hemoglobin levels is sustained for at least about 24 weeks after administration of LNP023 or a pharmaceutically acceptable salt thereof, e.g., LNP023 hydrochloride.

In an embodiment, the increase in hemoglobin levels is sustained for at least about 1 month, at least about 2 months, at least about 3 months, at least about 4 months, at least about 5 months, at least about 6 months, at least about 8 months, at least about 10 months, or at least about 12 months after administration of LNP023 or a pharmaceutically acceptable salt thereof, e.g., LNP023 hydrochloride.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

| List of abbreviations | |
|---|---|
| AE | Adverse Event |
| ALP | Alkaline Phosphatase |
| ALT | Alanine Aminotransferase |
| AST | Aspartate Aminotransferase |
| b.i.d. | bis in die/twice a day |
| BMF | Bone Marrow Failure |
| BTH | Breakthrough hemolysis |
| BUN | Blood Urea Nitrogen |
| CDS | Core Data Sheet |
| CK | Creatinine Kinase |
| CMO&PS | Chief Medical Office and Patient Safety |
| CO | Country Organization |
| COA | Clinical Outcome Assessment |
| CRF | Case Report/Record Form (paper or electronic) |
| CRO | Contract Research Organization |
| CSR | Clinical study report |
| CV | Coefficient of Variation |
| DBP | Diastolic Blood Pressure |
| DMC | Data Monitoring Committee |
| ECG | Electrocardiogram |
| EDC | Electronic Data Capture |
| EVH | Extravascular Hemolysis |
| eSAE | Electronic Serious Adverse Event |
| ESA | Erythropoiesis Stimulating Agent |
| eSource | Electronic Source |
| FSH | Follicle Stimulating Hormone |
| GCP | Good Clinical Practice |
| GCS | Global Clinical Supply |
| GGT | Gamma-glutamyl transferase |
| h | Hour |
| HIV | Human immunodeficiency virus |
| HRQoL | Health-Related Quality of Life |
| i.v. | intravenous |
| D3 | Investigator's Brochure |
| ICF | Informed Consent Form |
| ICH | International Council for Harmonization of Technical Requirements for Pharmaceuticals for Human Use |
| IEC | Independent Ethics Committee |
| IN | Investigator Notification |
| INR | International Normalized Ratio |
| IRB | Institutional Review Board |
| IRT | Interactive Response Technology |
| IVH | Intravascular Hemolysis |
| LDH | lactate dehydrogenase |
| LFT | Liver function test |
| LLOQ | lower limit of quantification |
| MAVE | Major Adverse Vascular Event |
| MedDRA | Medical dictionary for regulatory activities |
| mg | milligram(s) |
| mL | milliliter(s) |
| ORN | Off-site Research Nursing |
| PGIS | Patient Global Impression of Severity |
| p.o. | oral(ly) |
| PD | Pharmacodynamic(s) |
| PK | Pharmacokinetic(s) |
| PPD | Premature Participant Discontinuation |
| PRO | Patient Reported Outcomes |
| PT | prothrombin time |
| QD | Once a day |
| QMS | Quality Management System |
| QTcF | QT interval corrected by Fridericia's formula |
| RAP | The Report and Analysis Plan |
| RBC | red blood cell(s) |
| RDC | Remote Data Capture |
| REB | Research Ethics Board |
| RU | Resource Utilization |
| SAE | Serious Adverse Event |
| SAP | Statistical Analysis Plan |
| SBP | Systolic Blood Pressure |
| sCR | serum creatinine |
| SD | standard deviation |
| SUSAR | Suspected Unexpected Serious Adverse Reaction |
| TD | Study Treatment Discontinuation |
| ULN | upper limit of normal |
| WBC | white blood cell(s) |
| WHO | World Health Organization |
| WoC | Withdrawal of Consent |

| Glossary of terms | |
|---|---|
| Additional treatment | Medicinal products that may be used during the clinical trial as described in the protocol, but not as an investigational medicinal product (e.g. any background therapy) |
| Assessment | A procedure used to generate data required by the study |
| Biologic Samples | A biological specimen including, for example, blood (plasma, serum), saliva, tissue, urine, stool, etc. taken from a study participant |
| Cohort | A specific group of participants fulfilling certain criteria and generally treated at the same time |
| Control drug | A study drug (active or placebo) used as a comparator to reduce assessment bias, preserve blinding of investigational drug, assess internal study validity, and/or evaluate comparative effects of the investigational drug |

-continued

| Glossary of terms | |
|---|---|
| Dosage | Dose of the study treatment given to the participant in a time unit (e.g. 100 mg once a day, 75 mg twice a day) |
| Electronic Data Capture (EDC) | Electronic data capture (EDC) is the electronic acquisition of clinical study data using data collection systems, such as Web-based applications, interactive voice response systems and clinical laboratory interfaces. EDC includes the use of Electronic Case Report Forms (eCRFs) which are used to capture data transcribed from paper source forms used at the point of care |
| End of the clinical trial | The end of the clinical trial is defined as the last visit of the last participant or at a later point in time as defined by the protocol |
| Enrollment | Point/time of participant entry into the study at which informed consent must be obtained |
| Estimand | A precise description of the treatment effect reflecting the clinical question posed by the trial objective. It summarizes at a population-level what the outcomes would be in the same patients under different treatment conditions being compared. Attributes of an estimand include the population, variable (or endpoint) and treatment of interest, as well as the specification of how the remaining intercurrent events are addressed and a population-level summary for the variable. |
| Healthy volunteer | A person with no known significant health problems who volunteers to be a study participant |
| Intercurrent events | Events occurring after treatment initiation that affect either the interpretation or the existence of the measurements associated with the clinical question of interest. |
| Investigational drug/treatment | The drug whose properties are being tested in the study |
| Medication number | A unique identifier on the label of medication kits |
| Mis-randomized participants | Mis-randomized participants are those who were not qualified for randomization and who did not take study treatment, but have been inadvertently randomized into the study |
| Other treatment | Treatment that may be needed/allowed during the conduct of the study (i.e. concomitant or rescue therapy) |
| Part | A sub-division of a study used to evaluate specific objectives or contain different populations. For example, one study could contain a single dose part and a multiple dose part, or a part in participants with established disease and in those with newly-diagnosed disease |
| Participant | A trial participant (can be a healthy volunteer or a patient) |
| Participant number | A unique number assigned to each participant upon signing the informed consent. This number is the definitive, unique identifier for the participant and should be used to identify the participant throughout the study for all data collected, sample labels, etc. |
| Period | The subdivisions of the trial design (e.g. Screening, Treatment, Follow-up) which are described in the Protocol. Periods define the study phases and will be used in clinical trial database setup and eventually in analysis |
| Personal data | Participant information collected by the Investigator that is coded and transferred to Novartis for the purpose of the clinical trial. This data includes participant identifier information, study information and biological samples. |
| Premature participant withdrawal | Point/time when the participant exits from the study prior to the planned completion of all study drug administration and/or assessments; at this time all study drug administration is discontinued and no further assessments are planned |
| Randomization number | A unique identifier assigned to each randomized participant |
| Screen Failure | A participant who did not meet one or more criteria that were required for participation in the study |
| Source Data/Document | Source data refers to the initial record, document, or primary location from where data comes. The data source can be a database, a dataset, a spreadsheet or even hard-coded data, such as paper or eSource |
| Start of the clinical trial | The start of the clinical trial is defined as the signature of the informed consent by the first participant |
| Study treatment | Any drug or combination of drugs or intervention administered to the study participants as part of the required study procedures; includes investigational drug(s), control(s) or background therapy |
| Study treatment discontinuation | When the participant permanently stops taking any of the study drug(s) prior to the defined study treatment completion date (if any) for any reason; may or may not also be the point/time of study discontinuation |
| Treatment arm/group | A treatment arm/group defines the dose and regimen or the combination, and may consist of 1 or more cohorts. |
| Treatment of interest | The treatment of interest and, as appropriate, the alternative treatment to which comparison will be made. These might be individual interventions, combinations of interventions administered concurrently, e.g. as add-on to standard of care, or might consist of an overall regimen involving a complex sequence of interventions. This is the treatment of interest used in describing the related clinical question of interest, which might or might not be the same as the study treatment. |

-continued

| Glossary of terms | |
|---|---|
| Variable (or endpoint) | The variable (or endpoint) to be obtained for each participant that is required to address the clinical question. The specification of the variable might include whether the participant experiences an intercurrent event. |
| Withdrawal of study consent (WoC) | Withdrawal of consent from the study occurs only when a participant does not want to participate in the study any longer and does not allow any further collection of personal data |

Example 1. A Randomized, Multicenter, Active-Comparator Controlled, Open Label Trial to Evaluate Efficacy and Safety of LNP023 Hydrochloride, Administered Oral, Twice Daily in Adult Patients with PNH and Residual Anemia, Despite Treatment with an Intravenous Anti-C5 Antibody Purpose The purpose of this Phase 3 study in PNH patients presenting with residual anemia despite treatment with anti-C5 antibody, is to determine whether LNP023 hydrochloride is efficacious and safe for the treatment of PNH through demonstration of superiority of LNP023 hydrochloride compared to anti-C5 antibody treatment. This Phase 3 study has a 24-week randomized, active comparator controlled, open-label study period and a 24-week open-label extension period. Efficacy will be evaluated by the proportion of participants achieving the primary hemoglobin response criteria in the absence of red blood cell transfusions, as well as other hematological response endpoints, transfusion avoidance, breakthrough hemolysis rates and fatigue scores (FACIT-Fatigue, a patient reported outcome questionnaire).

The results of the analysis performed once the last participant has completed the 24-week Randomized treatment period will form the basis of the data package for regulatory filing.

Primary Objectives and Endpoints

The primary objectives are to:
1) demonstrate superiority of LNP023 hydrochloride compared to anti-C5 antibody treatment in the proportion of participants achieving a sustained increase from baseline in hemoglobin levels of ≥2 g/dL in the absence of red blood cell transfusions,
2) demonstrate superiority of LNP023 hydrochloride, compared to anti-C5 antibody treatment, in the proportion of participants achieving sustained Hb levels ≥12 g/dL in the absence of red blood cell transfusions.

Effect of treatment of LNP023 hydrochloride at a dose of 200 mg b.i.d. versus anti-C5 antibody treatment in PNH patients with residual anemia, regardless of discontinuation of study medication and occurrence of breakthrough hemolysis or Major Adverse Vascular Events (MAVEs), will be assessed on the odds of being a responder, with the endpoints defined as a composite of
  An increase in Hb levels from baseline ≥2 g/dL
  Hb levels ≥12 g/dL, where both endpoints will be assessed between Day 126 and Day 168 and of not requiring RBC transfusions between Day 14 and Day 168).

Secondary Objectives:

The secondary objectives are to:
1) demonstrate superiority of LNP023 hydrochloride, compared to anti-C5 antibody treatment in transfusion avoidance as the proportion of participants who remain free from transfusions by assessing the proportion of participants not receiving any packed red blood cell transfusions per protocol established criteria between Day 14 and Day 168;
2) demonstrate superiority of LNP023 hydrochloride, compared to anti-C5 antibody treatment, in average change in hemoglobin by assessing the change from baseline in hemoglobin (g/dL) as mean of visits between Day 126 and Day 168;
3) demonstrate superiority of LNP023 hydrochloride, compared to anti-C5 antibody treatment, in improving fatigue, using the FACIT-Fatigue questionnaire by assessing the change from baseline in FACIT-Fatigue scores as mean of visits between Day 126 and Day 168;
4) demonstrate superiority of LNP023 hydrochloride, compared to anti-C5 antibody treatment, in average change in reticulocyte counts by assessing the change from baseline in reticulocyte count (109/L) as mean of visits between Day 126 and Day 168;
5) demonstrate superiority of LNP023 hydrochloride, compared to anti-C5 antibody treatment, in average percent change in LDH by assessing the percent change from baseline in LDH levels (U/L) as mean of visits between Day 126 and Day 168;
6) demonstrate superiority of LNP023 hydrochloride, compared to anti-C5 antibody treatment, in the rate of breakthrough hemolysis (BTH) of participants with breakthrough hemolysis reported between Day 1 and Day 168;
7) assess rates of MAVEs (incl. thrombosis) of LNP023 hydrochloride, compared to anti-C5 antibody treatment occurring between Day 1 and Day 168.

Exploratory Objectives

The exploratory objectives are to:
1) assess safety and tolerability of LNP023 compared to anti-C5 treatment with safety evaluations including, adverse events/serious adverse events, safety laboratory parameters, vital signs etc.;
2) assess the effect of LNP023 compared to anti-C5 antibody treatment in hematological parameters, units of RBC transfusions and PNH signs and symptoms; hematological parameters (including RBCs, haptoglobin etc), bilirubin levels, units of packed RBC transfusions, and PNH signs & symptoms will be collected between Day 1 and Day 168 by the average of model derived estimates for visits between Day 126 and Day 168;
3) assess the effect of LNP023, compared to anti-C5 antibody treatment, in patient-reported overall fatigue severity and health-related quality of life; change in patient-reported outcomes scores for PGIS, EORTC QLQ-C30, and EQ-5D-5L collected between Day 1 and Day 168 with focus on comparing treatments on the average of model derived estimates for visits between Day 126 and Day 168 will be assessed;

4) assess the effect of LNP023, compared to anti-C5 treatment, on C3 fragment deposition on PNH type red blood cells and PNH clone size; the percentage of C3d positive PNH-type red blood cells collected between Day 1 and Day 168 will be determined, and PNH type II & III red blood cells and total PNH clone size (percentage) of red blood cells will be collected between Day 1 and Day 168;

5) characterize the PK of LNP 023 in the PNH population based on PK exposure data; and 6) assess the effect of LNP023 compared to anti-C5 treatment in the utilization of Health Care resources based on the occurrence of hospitalizations, rehospitalizations, and emergency room visits between Day 1 and Day 168.

Study Design

This study is a multi-center, randomized, open-label, active comparator-controlled, parallel group study, which is comprised of three periods (see FIG. 1):

A screening period lasting up to 8 weeks (unless there is a need to extend it for vaccinations required for inclusion)

A 24-week randomized, open-label, active controlled, parallel group treatment period for the primary efficacy and safety analyses A 24-week open-label, LNP023 hydrochloride treatment extension period The study will enroll PNH patients with residual anemia, defined as hemoglobin <10 g/dL, despite stable regimen of anti-C5 antibody treatment (eculizumab or ravulizumab) in the last 6 months before Randomization, with approximately 40% of participants having received at least 1 packed-RBC transfusions in the 6 months prior to randomization. A total of approximately 91 participants will be randomized in the trial. All participants must provide written informed consent prior to start of any study-related activities. The study design is shown in FIG. 1.

Study Design Rationale

The Phase 3 study is designed as a multicenter, open-label, randomized, active-comparator controlled, parallel group study for demonstration of superiority of LNP023 hydrochloride at a dose of 200 mg b.i.d. orally compared to intravenous anti-C5 antibody treatment on hematological response parameters and patient reported outcome measures for fatigue, in patients with PNH that present with residual anemia despite treatment with a stable regimen of anti-C5 antibody treatment (SoC).

Screening

Patient eligibility will be determined before the start of the run-in period (based on the assessments performed at Visit 1). Inclusion and exclusion criteria will be assessed to verify participants' eligibility for enrollment into the study. The screening assessments are listed in FIG. 2.

Participants should be vaccinated at the time of screening. Vaccines should cover as many serotypes as possible (including meningococcal serotypes A, C, Y, W-135 and B). To minimise patient burden, the use of multivalent vaccines is recommended as locally available and per local guidelines and regulations (e.g. quadrivalent vaccine for *N. meningitidis* which covers serotypes A, C, Y and W-135 and Pneumovax-23 which covers 23 *S. pneumoniae* serotypes).

To fulfill the hemoglobin eligibility criterion, participants will have two different samples collected during the screening period and tested by the central laboratory with the mean <−10 g/dL, prior to Randomization. In case the participant has received a RBC transfusion following the initial sample collection, the patient is eligible based on the initial central hemoglobin value if <10 g/dL.

Participants who meet the eligibility criteria at screening will be stratified based on the type of prior anti-C5 antibody treatment (eculizumab or ravulizumab) and based on the transfusion history as reported during the last 6 months prior to Randomization (i.e. transfusion received/not received). It is assumed that approximately 40% of randomized participants having received at least one packed red blood cell (pRBC) transfusion in the 6 months prior to randomization.

Randomization and Randomized Treatment Period

Participants will be randomized to one of the two treatment arms in a 8:5 ratio to either LNP023 hydrochloride monotherapy at a dose of 200 mg orally b.i.d. (approximately 56 participants), or i.v. anti-C5 antibody treatment (approximately 35 participants continuing with the same regimen during the Randomized treatment period as they were on prior to randomization), respectively.

Treatment will start on the first day of dosing (Day 1) and continue for 24 weeks with study visits and corresponding assessments according to schedule described in FIG. 2. Participants assigned to the comparator arm will continue receiving the same type, and regimen of anti-C5 antibody treatment as received prior to randomization, while those randomized to the LNP023 hydrochloride treatment arm will start taking LNP023 hydrochloride at dose of 200 mg b.i.d.

Considering that some patients may present with very low hemoglobin levels (e.g. <7 g/dL), and thereby require a red blood cell transfusion during the first two weeks of the Randomized treatment period, transfusions administered during these first 2 weeks will not be considered for the transfusion avoidance definition.

Extension Period

The participants randomized to the active comparator arm will be offered to switch to LNP023 hydrochloride on Day 168 (Week 24 visit) and enter the Extension treatment period, after receiving a last dose of anti-C5 (eculizumab or ravulizumab) antibody treatment. For participants in the comparator arm not agreeing to switch treatment, Week 24 will be the End of Study visit for the trial and there will be no participation in the Extension period. For participants agreeing to switch to oral LNP023 hydrochloride, the Extension treatment will start on the day after completion of the Week 24 visit.

After switching to LNP023 hydrochloride, the participants in the comparator arm will follow study visits and assessments according to the schedule described in FIG. 3.

Study Population

Patients diagnosed with PNH, who are treated with a stable regimen of anti-C5 monoclonal antibody treatment (Standard of Care; either eculizumab or ravulizumab) for at least 6 months prior to Randomization, but still presenting with residual anemia (i.e., Hb<10 g/dL) will be enrolled. Approximately 40% of participants having received at least 1 packed-RBC transfusions in the 6 months prior to randomization are to be enrolled.

Key Inclusion Criteria

Participants eligible for inclusion in this study must meet all of the following criteria:

1. Male and female participants ≥18 years of age with a diagnosis of PNH confirmed by high-sensitivity flow cytometry with RBCs and/or confirmed WBCs granulocyte/monocyte clone size ≥10%
2. Stable regimen (dose and intervals) of anti-C5 antibody treatment (either eculizumab or ravulizumab) for at least 6 months prior to Randomization
3. Mean hemoglobin level <10 g/dL 4. Over a minimum of 4 months before Screening visit,
5. Confirmed by central laboratory assessment during Screening
6. Vaccination against *Neisseria meningitidis* infection is required prior to the start of treatment. If the patient has not been previously vaccinated, or if a booster is required, vaccine should be given, as available and according to local regulations, at least 2 weeks prior to first dosing.
7. If not received previously, vaccination against *Streptococcus pneumoniae* and *Haemophilus influenzae* infections should be given, if available and according to local regulations. The vaccines should be given at least 2 weeks prior to first LNP023 hydrochloride dosing.

Key Exclusion Criteria

Participants meeting any of the following criteria are not eligible for inclusion in this study.
1. Participants on a stable eculizumab dose but with a dosing interval of 11 days or less
2. Known or suspected hereditary complement deficiency at screening
3. History of hematopoietic stem cell transplantation
4. Patients with laboratory evidence of bone marrow failure (reticulocytes <100×109/L; platelets <30×109/L; neutrophils <500×106/L).
5. Active systemic bacterial, viral or fungal infection within 14 days prior to study drug administration
6. A history of recurrent invasive infections caused by encapsulated organisms, e.g. meningococcus or pneumococcus.
7. Major concurrent comorbidities including but not limited to severe kidney disease (e.g., dialysis), advanced cardiac disease (e.g., NYHA class IV), severe pulmonary disease (e.g., severe pulmonary hypertension (WHO class IV)), or hepatic disease (e.g., active hepatitis) that in the opinion of the investigator precludes participant's participation in the study.

Treatment

Participants will be randomized in an 8:5 ratio to either LNP023 hydrochloride monotherapy given orally b.i.d. (where the anti-C5 antibody treatment will be stopped—See below for timing), or intravenous anti-C5 antibody treatment (continuing with the same dose as that received prior to Randomization).

LNP023 Hydrochloride First Administration (Day 1 Visit)

The timing of the first LNP023 hydrochloride administration will provide a seamless switch from prior anti-C5 antibody treatment to LNP023 hydrochloride, allowing for some overlap of exposure to anti-C5 antibody treatment when starting the oral agent while limiting the potential risk of breakthrough hemolysis, as the LNP023 hydrochloride exposure builds-up.

First LNP023 hydrochloride dose administration of participants on prior eculizumab regimen should occur at the start of the 2nd week of the 2-week dosing interval (i.e, preferably around days 7-to-8 after last infusion)

First LNP023 hydrochloride dose administration for participants on prior ravulizumab regimen should occur at the beginning of the $7^{th}$ week of the 8-week dosing interval (preferably around days 41-to-43 after the last infusion)

Participants will then continue taking 200 mg LNP023 hydrochloride b.i.d. monotherapy.

Anti-O5 First Administration in the Study (Day 1 Visit)

Participants assigned to the comparator arm will continue receiving the anti-C5 infusion as per their stable regimen. However, the day of the next administration of anti-C5 for the 'study start' should coincide with 'Day 1' study day. The investigator is encouraged to 'count back' from the schedule date for the planned infusion.

Extension Period: LNP023 Hydrochloride Administration for Comparator Group

At Week 24 visit, participants in the comparator arm will receive the last anti-C5 infusion, and will start with the first LNP023 hydrochloride dose administration the morning after the visit (Day 169).

With participants starting in the Extension period taking LNP023 hydrochloride starting on Day 169, the visit schedule will be harmonized, with the exception of Day 182, where only participants formerly assigned to the comparator arm will return 7 days after first LNP023 hydrochloride administration, for PK and safety assessments.

Study Treatment

In this study, the "study treatment" includes the investigational drug, LNP023 hydrochloride, and the active comparators of anti-C5 antibodies (either eculizumab or ravulizumab).

TABLE 1

| Investigational/Comparator | Pharmaceutical dosage form | Route of administration | Supply type |
| --- | --- | --- | --- |
| LNP023 hydrochloride, 200 mg | Hard gelatin capsule | Oral use | Open label, patient specific kits |
| Eculizumab, 300 mg/30 mL | Concentrate solution for infusion | Intravenous infusion | Open label, vial |
| Ravulizumab, 300 mg/30 mL | Concentrate solution for infusion | Intravenous infusion | Open label, vial |
| LNP023 hydrochloride, 10* mg | Hard gelatin capsule | Oral use | Open label, patient specific kits |

*used only during tapering down of LNP023 hydrochloride dose

The investigational drug, LNP023 hydrochloride as 10 mg and 200 mg capsules, will be prepared by Novartis and supplied to investigator sites as open-label participant packs. Eculizumab and ravulizumab will be provided locally by the study site, subsidiary or designee as commercially available or by Novartis, in each participating country according to local practices and local regulations.

Treatment Duration

The duration of the Randomized Treatment period is 24 weeks. If a participant's treatment with LNP023 hydrochloride is discontinued (e.g. due to lack of efficacy) and patient is switched back to the prior anti-C5 antibody treatment, every effort will be made to continue with the study assessments up to the Week 24 visit.

The Extension period will last up to 24 weeks, where participants randomized to LNP023 hydrochloride arm during the Randomized treatment period will continue with LNP023 hydrochloride treatment, and participants randomized to anti-C5 arm will be offered to switch to LNP023 hydrochloride monotherapy.

Dose and Duration of Treatment Rationale

The dose of 200 mg LNP023 hydrochloride b.i.d. as continuous treatment has been selected for this Phase 3 study primarily based on the available efficacy and safety data obtained at the time of interim analyses from the two ongoing Phase 2 PNH studies (ClinicalTrials.gov Identifier: NCT03439839 and NCT03896152) and is supported by PKPD modeling results.

In the CLNP023X2201 study in patients with active hemolysis despite treatment with eculizumab, LNP023 hydrochloride at a dose of 200 mg b.i.d. was administered to 10 PNH participants (cohort 1) and at a dose of 50 mg b.i.d. to 6 PNH participants (cohort 2). An interim analysis (IA) was conducted after 10 participants (cohort 1) completed at least 12 weeks of treatment with LNP023 hydrochloride 200 mg b.i.d. add-on treatment to eculizumab.

In the Phase 2 study (NCT03439839) in anti-C5 antibody treatment naive patients, participants received LNP023 hydrochloride monotherapy with sequential dose increments at Week 4 from LNP023 hydrochloride 25 mg b.i.d. to 100 mg b.i.d (sequence 1) or LNP023 hydrochloride 50 mg b.i.d. to 200 mg b.i.d. (sequence 2). An IA was conducted after 8 patients were randomized and 7 patients completed Week 8 visit assessments.

The dose of 200 mg b.i.d. is expected to provide optimal efficacy required for PNH as monotherapy with an adequate safety profile based on the following key findings of the two interim analyses:

Participants treated with LNP023 hydrochloride 200 mg b.i.d. (as add-on to eculizumab) had clinical benefits not achieved with eculizumab that included control of IVH demonstrated by LDH reduction, control of EVH demonstrated by reduction of bilirubin, reticulocytes and increase in haptoglobin resulting in normalization of hemoglobin in the majority of patients in the absence of red blood cell transfusions. The hematological response participants achieved with LNP023 hydrochloride 200 mg b.i.d. add-on therapy was maintained with LNP023 hydrochloride monotherapy during the extension period (at the time of the IA) when eculizumab treatment was discontinued in 5/10 participants who continued with LNP023 hydrochloride monotherapy. Following the IA, two additional participants discontinued eculizumab treatment. C3 deposition was fully reversed by addition of LNP023 hydrochloride at a dose of 200 mg b.i.d. and survival of PNH red blood cells prolonged further supporting control of EVH by LNP023 hydrochloride at a dose of 200 mg b.i.d. There was sustained inhibition of the complement alternative pathway and profound and sustained reduction of Fragment Bb demonstrating target engagement.

Participants receiving LNP023 hydrochloride monotherapy showed that LNP023 hydrochloride at dose levels ≥25 mg b.i.d. had LDH reduction of more than 60% from baseline in all participants and early transfusion-free hemoglobin increase in the majority of participants. Other hemolysis relevant laboratory values indicated that LNP023 hydrochloride administered as monotherapy controls both, intra (LDH reduction) and extravascular hemolysis (decrease of reticulocytes and bilirubin, increase in haptoglobin).

Preliminary information from cohort 2 in the Phase 2 study (NCT03439839) suggests that the LNP023 hydrochloride dose of 50 mg b.i.d. may not provide optimal efficacy required for LNP023 hydrochloride monotherapy in PNH. There was suboptimal response in three participants requiring up-titration to the dose of 200 mg b.i.d.

LNP023 hydrochloride at a dose of 200 mg b.i.d. was safe and well tolerated by participants in both studies in PNH, as well as at the same dose in patients with IgA nephropathy (study CLNP023X2203) and C3 glomerulopathy (CLNP023X2202), supporting its use in this Phase 3 study.

The exposure-response model developed with data from the First In Human (FIH) study with LNP023 hydrochloride in healthy volunteers predicts that a dose of about 200 mg b.i.d. would be needed to achieve >90% inhibition of the alternative pathway (Wieslab assay) in >70% of subjects. Given the risk of hemolysis and breakthroughs in cases of insufficient inhibition of complement activity, full inhibition is desired and modelling results provide additional support for the choice of the dose of 200 mg b.i.d. for PNH.

Prohibited Medication

Use of the treatments listed below are not allowed during LNP023 hydrochloride administration.

Live vaccines are prohibited for the entire study treatment duration

Gemfibrozil (a potent inhibitor of metabolizing enzymes CYP2C8, UGT1A and liver uptake transporter OATP1B1) must be interrupted 48 hours before first LNP023 hydrochloride dose until end of LNP023 hydrochloride treatment (and replaced with another appropriate medication used for that indication).
  If re-initiated during the study when LNP023 hydrochloride is administered, discontinue the prohibited treatment immediately Clopidogrel (a strong inhibitor of CYP2C8) must be interrupted 7 days before first LNP023 hydrochloride dose until end of LNP023 hydrochloride treatment (and replaced with another appropriate medication used for that indication.)
  If re-initiated during the study, when LNP023 hydrochloride is administered, discontinue the prohibited treatment immediately In either case of interruption during LNP023 hydrochloride administration, the participant should continue in the study and safety/tolerability be closely monitored.

Visit Schedule and Assessments

The assessment schedule (FIGS. 2 and 3) lists all of the assessments when they are performed. During the Screening period, mean hemoglobin <10 g/dL will be confirmed by central laboratory assessment prior to Randomization evaluated by two hemoglobin measurements, (mean <10 g/dL), two up to eight weeks apart; or by one hemoglobin measurement (<10 g/dL) from the first assessment for patients receiving a pRBC transfusion after the first assessment. If a participant receives a packed-RBC transfusion following the first assessment carried out for the Screening visit (central laboratory), he/she will be eligible without an additional hemoglobin assessment by the central laboratory.

Efficacy

Blood samples for hematology, clinical chemistry and $C3^+$ RBCs, PNH type II/III RBCs and PNH clone size will be collected according to the schedule in FIG. 2 for the Randomized Treatment period.

The following laboratory parameters will be assessed: Hemoglobin (and also haptoglobin), reticulocyte count and bilirubin (as makers for extravascular hemolysis), LDH (as a marker for intravascular hemolysis), RBCs, PNH clone size, PNH type RBCs as well as $C3^+$ on PNH type RBCs.

During the Extension period, the assessment will be carried out as per the schedule in FIG. 3.

Red Blood Cell Transfusion

The need for administration of red blood cell transfusion will be monitored continuously during the Randomized Treatment period.

To standardize criteria for administration, transfusion criteria have been established and will apply starting from Day 1 of the study.

Packed RBC transfusions will be administered to participants in the following cases:

Hemoglobin level between <9 g/dL with adequately severe signs/and or symptoms to warrant a transfusion Hemoglobin of <7 g/dL, regardless of presence of clinical signs and symptoms Breakthrough Hemolysis The occurrence of breakthrough hemolysis will be monitored continuously during the Randomized treatment period. The criteria for clinical breakthrough is defined in Table 2 below if either one of the two clinical criteria is met. In contrast to clinical breakthrough as defined, the isolated laboratory evidence of increased intravascular hemolysis, without meaningful decrease in hemoglobin and without other clinical signs or symptoms of hemolysis (see Table 2), is defined as subclinical breakthrough hemolysis.

TABLE 2

Breakthrough definition

| | Clinical criteria Hemoglobin levels | Signs or symptoms | Laboratory criteria LDH level |
|---|---|---|---|
| Clinical breakthrough * | Decrease equal to or more than 2 g/dL (compared to the latest assessment, or within 15 days) | Gross hemoglobinuria, painful crisis, dysphagia or any other significant clinical PNH-related signs & symptoms | >1.5-times ULNand increased as compared to the last 2 assessments |
| Subclinical breakthrough | Decrease less than 2 g/dL (compared to the latest assessment, or within 15 days) | No clinical signs or symptoms, except moderate hemoglobinuria | >1.5-times ULN and increased as compared to the last 2 assessments |

LDH: lactate dehydrogenase; UNN: Upper Limit of Normal;
* The breakthrough is defined clinical if either one of the two clinical criteria is demonstrated, in presence of laboratory evidence of intravascular hemolysis (LDH level)

During the Extension period, breakthrough hemolysis will be monitored continuously until the end of study visit following the same criteria and guidance described above.

Patient Reported Outcomes (PRO)—FACIT-Fatigue

The FACIT-Fatigue is a 13-item questionnaire that assesses self-reported fatigue and its impact upon daily activities and function. It will be used to assess patient-reported fatigue. FACIT-Fatigue is one of many different FACIT scales part of a collection of Health-Related Quality of Life (HRQoL) questionnaires referred to as the FACIT Measurement System (Webster K, Cella D, and Yost K. (2003). The functional assessment of chronic illness therapy (FACIT) measurement system: properties, applications, and interpretation. Health Qual Life Outcomes; 16:1-79; Yellen S B, et al. (1997). Measuring fatigue and other anemia-related symptoms with functional assessment of cancer therapy (FACT) measurement system. J Pain Symmptom Manage; 13:633-74). The use of the FACIT-F in PNH patients has been reported in several publications and is sensitive to changes in disease status, allowing demonstration of statistically significant and clinically meaningful results (Brodsky R A, et al. (2008) Multicenter phase 3 study of the complement inhibitor eculizumab for the treatment of patients with paroxysmal nocturnal hemoglobinuria. Blood; 4:1840-1847; Ueda Y, Obara N, et al. (2018). Effects of eculizumab treatment on quality of life in patients with paroxysmal nocturnal hemoglobinuria in Japan. Int J Hematol; 107:656-665; Kulasekararaj A G, et al. (2019) Ravulizumab (ALXN1210) vs eculizumab in C5-inhibitor-experienced adult patients with PNH: the 302 study. Blood; 133:540-549). All FACIT scales are scored so that a high score is better. As each of the 13 items of the FACIT-F Scale ranges from 0-4, the range of possible scores is 0-52, with 0 being the worst possible score and 52 the best.

PNH-Related Signs & Symptoms

PNH signs and symptoms will be collected according to FIG. 2 for the Randomized Treatment period. The investigator (or designee) will record the presence of the following signs and symptoms:
Reddish or cola-colored urine especially in the morning/ or hemoglobinuria
Feeling weak or tired
Shortness of breath/dyspnea
Dysphagia/difficulty swallowing
Chest pain
Abdominal/belly pain
Erectile dysfunction/impotency Pharmacokinetics PK samples will be collected at the visits defined in the assessment schedule (FIGS. 2 and 3). Pharmacokinetic (PK) samples will be obtained and evaluated in all participants taking LNP023 hydrochloride. LNP023 hydrochloride will be determined by a validated LC-MS/MS method; the anticipated Lower Limit of Quantification (LLOQ) is 1.0 ng/mL. Metabolites (as needed) may be determined as appropriate. Concentrations will be expressed in mass per volume units (ng/mL) and will refer to the anhydrous free base.

Study Discontinuation and Completion

Discontinuation of study treatment for a participant occurs when study treatment is stopped earlier than the protocol planned duration and can be initiated by either the participant or the investigator.

Close monitoring of participants for signs and symptoms of hemolysis should be performed upon LNP023 hydrochloride discontinuation. It is recommended to monitor at minimum for: increase in LDH, decrease in hemoglobin level and PNH clone size, increase in serum creatinine, thrombosis, and change in mental status. If serious hemolysis occurs, the Investigator should consider the following supportive treatments (and record them in the appropriate CRF pages):
Blood transfusion (packed RBCs),
Or exchange transfusion if the PNH RBCs are >50% of the total RBCs by flow cytometry
Corticosteroids
Anticoagulation
Any other supportive treatment or therapy as judged by the investigator.

If treatment with LNP023 hydrochloride has to be discontinued prematurely but it is not warranted to immediately discontinue LNP023 hydrochloride treatment, i.e. discontinuation due to participant/guardian decision or confirmed pregnancy, it is recommended to promptly re-initiate the anti-C5 antibody treatment, as judged by the investigator. In addition, it should be considered to taper down LNP023 hydrochloride over a period of 14 days, as follows:
3 capsules of 10 mg LNP023 hydrochloride taken in the evening (once daily) for 7 days
1 capsule of 10 mg LNP023 hydrochloride taken in the evening (once daily) for 7 days

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of treating paroxysmal nocturnal hemoglobinuria (PNH) in a subject in need thereof, the method comprising orally administering to the subject 4-((2S,4S)-

(4-ethoxy-1-((5-methoxy-7-methyl-1H-indol-4-yl)methyl) piperidin-2-yl))benzoic acid or a pharmaceutically acceptable salt thereof, at a dose of about 200 mg twice daily (b.i.d.), to thereby treat the subject, wherein the dose refers to an amount of anhydrous free base of 4-((2S,4S)-(4-ethoxy-1-((5-methoxy-7-methyl-1H-indol-4-yl)methyl)piperidin-2-yl))benzoic acid.

2. The method of claim 1, wherein the subject has been previously treated with an anti-C5 therapy prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof.

3. The method of claim 2, wherein the anti-C5 therapy is an anti-C5 monoclonal antibody therapy.

4. The method of claim 1, wherein the subject has residual anemia.

5. The method of claim 1, wherein hemoglobin levels, haptoglobin levels, reticulocyte levels, and/or bilirubin levels of the subject, are evaluated prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof.

6. The method of claim 5, wherein the hemoglobin levels of the subject are less than or equal to about 10 g/dL, prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof.

7. The method of claim 1, wherein treating PNH comprises increasing hemoglobin levels in the subject as compared to hemoglobin levels in the subject prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof.

8. The method of claim 1, wherein treating PNH comprises normalizing intravascular hemolysis (IVH) and/or extravascular hemolysis (EVH) in the subject.

9. The method of claim 8, wherein normalizing IVH and/or EVH hemolysis comprises increasing the haptoglobin level, decreasing reticulocytes level, or decreasing bilirubin level, in the subject as compared to baseline.

10. The method of claim 1, wherein treating PNH comprises treating PNH associated hemolysis.

11. The method of claim 1, wherein treating PNH comprises reducing C3 deposition in the subject.

12. The method of claim 1, wherein treating PNH comprises increasing red blood cell (RBC) survival in the subject.

13. The method of claim 1, wherein treating PNH comprises reducing Fragment Bb level in the subject.

14. The method of claim 1, wherein treating PNH comprises increasing hemoglobin levels in the subject by about 2 g/dL or more as compared to baseline.

15. The method of claim 1, wherein treating PNH comprises achieving a sustained increase in hemoglobin level.

16. The method of claim 1, wherein treating PNH comprises achieving a sustained increase in hemoglobin level to greater than or equal to about 12 g/dL.

17. The method of claim 1, wherein treating PNH comprises increasing hemoglobin levels in the subject in the absence of receiving one or more red blood cell (RBC) transfusion(s).

18. The method of claim 1, wherein the subject has received RBC transfusions.

19. The method of claim 1, wherein the subject has been vaccinated prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof, and the prior vaccination is against *Neisseria meningitidis* (types A, C, Y and W-135).

20. The method of claim 1, wherein efficacy of treatment is determined by measuring the hemoglobin levels in the subject as compared to baseline.

21. The method of claim 1, wherein treating PNH comprises achieving a sustained increase in hemoglobin level after about 4 weeks of administering to the subject 4-((2S,4S)-(4-ethoxy-1-((5-methoxy-7-methyl-1H-indol-4-yl) methyl)piperidin-2-yl))benzoic acid or a pharmaceutically acceptable salt thereof.

22. The method of claim 1, comprising orally administering to the subject 4-((2S,4S)-(4-ethoxy-1-((5-methoxy-7-methyl-1H-indol-4-yl)methyl)piperidin-2-yl))benzoic acid hydrochloride.

23. The method of claim 8, comprising orally administering to the subject 4-((2S,4S)-(4-ethoxy-1-((5-methoxy-7-methyl-1H-indol-4-yl)methyl)piperidin-2-yl))benzoic acid hydrochloride.

24. The method of claim 14, comprising orally administering to the subject 4-((2S,4S)-(4-ethoxy-1-((5-methoxy-7-methyl-1H-indol -4-yl)methyl)piperidin-2-yl))benzoic acid hydrochloride.

25. The method of claim 16, comprising orally administering to the subject 4-((2S,4S)-(4-ethoxy-1-((5-methoxy-7-methyl-1H-indol-4-yl)methyl)piperidin-2-yl))benzoic acid hydrochloride.

26. The method of claim 17, comprising orally administering to the subject 4-((2S,4S)-(4-ethoxy-1-((5-methoxy-7-methyl-1H-indol-4-yl)methyl)piperidin-2-yl))benzoic acid hydrochloride.

27. The method of claim 19, comprising orally administering to the subject 4-((2S,4S)-(4-ethoxy-1-((5-methoxy-7-methyl-1H-indol -4-yl)methyl)piperidin-2-yl))benzoic acid hydrochloride.

28. The method of claim 6, comprising orally administering to the subject 4-((2S,4S)-(4-ethoxy-1-((5-methoxy-7-methyl-1H-indol-4-yl)methyl)piperidin-2-yl))benzoic acid hydrochloride.

29. The method of claim 6, wherein treating PNH comprises increasing hemoglobin levels in the subject by about 2 g/dL or more as compared to baseline.

30. The method of claim 6, wherein the subject has been vaccinated prior to administration of 4-((2S,4S)-(4-ethoxy-1-((5-methoxy-7-methyl-1H-indol -4-yl)methyl)piperidin-2-yl))benzoic acid or a pharmaceutically acceptable salt thereof, and the prior vaccination is against *Neisseria meningitidis* (types A, C, Y and W-135).

31. The method of claim 6, wherein treating PNH comprises increasing hemoglobin levels in the subject in the absence of receiving one or more RBC transfusion(s).

32. The method of claim 14, wherein the subject has been vaccinated prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof, and the prior vaccination is against *Neisseria meningitidis* (types A, C, Y and W-135).

33. The method of claim 14, wherein treating PNH comprises increasing hemoglobin levels in the subject in the absence of receiving one or more RBC transfusion(s).

34. The method of claim 17, wherein the subject has been vaccinated prior to administration of 4-((2S,4S)-(4-ethoxy-1-((5-methoxy-7-methyl-1H-indol-4-yl)methyl)piperidin-2-yl))benzoic acid or a pharmaceutically acceptable salt thereof, and the prior vaccination is against *Neisseria meningitidis* (types A, C, Y and W-135).

35. The method of claim 32, comprising orally administering to the subject 4-((2S,4S)-(4-ethoxy-1-((5-methoxy-7-methyl-1H-indol-4-yl)methyl)piperidin-2-yl))benzoic acid hydrochloride.

36. The method of claim 33, comprising orally administering to the subject 4-((2S,4S)-(4-ethoxy-1-((5-methoxy-7-methyl-1H-indol-4-yl)methyl)piperidin-2-yl))benzoic acid hydrochloride.

37. The method of claim 34, comprising orally administering to the subject 4-((2S,4S)-(4-ethoxy-1-((5-methoxy-7-methyl-1H-indol-4-yl)methyl)piperidin-2-yl))benzoic acid hydrochloride.

38. The method of claim 37, wherein treating PNH further comprises increasing hemoglobin levels in the subject by about 2 g/dL or more as compared to baseline.

* * * * *